US011364480B2

(12) United States Patent
Ley et al.

(10) Patent No.: US 11,364,480 B2
(45) Date of Patent: Jun. 21, 2022

(54) CHROMATOGRAPHY MEDIUM WITH BOUND MICROGLOBULES AND METHOD FOR THE PREPARATION THEREOF

(71) Applicant: Sartorius Stedim Biotech GmbH, Göttingen (DE)

(72) Inventors: Adrian Ley, Göttingen (DE); Florian Taft, Göttingen (DE); Jan Schwellenbach, Göttingen (DE); Louis Villain, Hannover (DE)

(73) Assignee: Sartorius Stedim Biotech GmbH, Gottingen (DE)

( * ) Notice: Subject to any disclaimer, the term of this patent is extended or adjusted under 35 U.S.C. 154(b) by 350 days.

(21) Appl. No.: 16/479,559

(22) PCT Filed: Jan. 16, 2018

(86) PCT No.: PCT/EP2018/051016
§ 371 (c)(1),
(2) Date: Jul. 19, 2019

(87) PCT Pub. No.: WO2018/137975
PCT Pub. Date: Aug. 2, 2018

(65) Prior Publication Data
US 2019/0358609 A1    Nov. 28, 2019

(30) Foreign Application Priority Data
Jan. 24, 2017    (DE) ..................... 10 2017 000 631.8

(51) Int. Cl.
| | | |
|---|---|---|
| *B01J 20/26* | (2006.01) | |
| *B01J 20/28* | (2006.01) | |
| *B01J 20/286* | (2006.01) | |
| *B01J 20/32* | (2006.01) | |
| *C07K 1/22* | (2006.01) | |

(52) U.S. Cl.
CPC ........... *B01J 20/261* (2013.01); *B01J 20/267* (2013.01); *B01J 20/286* (2013.01); *B01J 20/28019* (2013.01); *B01J 20/28026* (2013.01); *B01J 20/28097* (2013.01); *B01J 20/3206* (2013.01); *B01J 20/327* (2013.01); *B01J 20/3276* (2013.01); *B01J 20/3278* (2013.01); *B01J 20/3282* (2013.01); *C07K 1/22* (2013.01); *B01J 2220/445* (2013.01)

(58) Field of Classification Search
CPC ........ B01J 20/26; B01J 20/261; B01J 20/267; B01J 20/28019; B01J 20/28026; B01J 20/28097; B01J 20/286; B01J 20/3206; B01J 20/327; B01J 20/3276; B01J 20/3278; B01J 20/3282; B01J 2220/445; C07K 1/22

USPC ......................................................... 502/402
See application file for complete search history.

(56) References Cited

U.S. PATENT DOCUMENTS

| | | |
|---|---|---|
| 6,451,260 B1 | 9/2002 | Düsterhöft et al. |
| 2005/0115890 A1 | 6/2005 | Demmer et al. |
| 2012/0024792 A1 | 2/2012 | Deetz et al. |

FOREIGN PATENT DOCUMENTS

| | | |
|---|---|---|
| DE | 103 44 820 A1 | 4/2005 |
| DE | 10 2008 055 821 A1 | 10/2009 |
| DE | 10 2013 017 014 A1 | 4/2015 |
| EP | 0 538 315 B1 | 12/1995 |
| JP | H07500363 A | 1/1995 |
| JP | H07507587 A | 8/1995 |
| JP | 2002513323 A | 5/2002 |
| WO | WO 92/15637 | 9/1992 |
| WO | WO 93/25594 | 12/1993 |
| WO | WO 98/37949 | 9/1998 |
| WO | WO 2010/142363 A1 | 12/2010 |

OTHER PUBLICATIONS

Office Action for Japanese Patent Application No. 2019-539796, dated Oct. 20, 2020 (w/English translation).
Office action for Chinese Application No. 201880008372.5 dated Sep. 3, 2021, and English translation, 14 pages.
Shukla et al., "Graft-copolymerization of glycidyl methacrylate onto cotton cellulose"; Department of Chemical Technology, University of Bombay, Matunga, Bombay; Journal of Applied Polymer Science, vol. 54, 279-288 (1994).
International Search Report dated Apr. 13, 2018, issued by the European Patent Office in corresponding Patent Cooperation Treaty Application No. PCT/EP2018/051016.
Translation of International Search Report dated Apr. 13, 2018, issued by the European Patent Office in corresponding Patent Cooperation Treaty Application No. PCT/EP2018/051016.
Written Opinion dated Apr. 13, 2019, issued by the European Patent Office in corresponding Patent Cooperation Treaty Application No. PCT/EP2018/051016.

*Primary Examiner* — Edward M Johnson
(74) *Attorney, Agent, or Firm* — Klarquist Sparkman, LLP

(57) ABSTRACT

A chromatography medium includes a porous matrix and nonporous globules bound on the inner and outer surfaces of the porous matrix. The average radius of the microglobules is not more than 30% of the average pore diameter of the porous matrix. The chromatography medium can be used in affinity chromatography. A method for preparing the chromatography medium may include providing a porous starting matrix, providing a polymerization solution, and initiating polymerization of the polymerization solution in the presence of the porous starting matrix to form insoluble nonporous microglobules that are bound to the inner and outer surfaces of the porous starting matrix.

15 Claims, 8 Drawing Sheets

CHROMATOGRAPHY MEDIUM WITH BOUND MICROGLOBULES AND METHOD FOR THE PREPARATION THEREOF

CROSS REFERENCE TO RELATED APPLICATIONS

This is the U.S. National Stage of International Application No. PCT/EP2018/051016, filed Jan. 16, 2018, which was published in English under PCT Article 21(2), which in turn claims the benefit of German Application No. 10 2017 000 631.8, filed Jan. 24, 2017, which application is incorporated herein in its entirety.

The present invention relates to a chromatography medium which can be used in affinity chromatography and to a method for the preparation thereof.

In downstream processing, protein A affinity chromatography is an important method for the purification of antibodies owing to high efficiency. High degrees of purity of the antibody are achieved in a single step, and this distinguishes said method both economically and environmentally from other purification methods. As in the case of all chromatographic methods for preparation purposes, the productivity of a chromatographic medium is of critical importance. In particular, this is made up of the flow rate allowed by the medium (permeability) and of the dynamic binding capacity. However, the chromatography media hitherto known in the prior art exhibit either a low flow rate or low permeability (e.g., protein A gel columns) or a low dynamic binding capacity (e.g., protein A membrane adsorbers).

In the prior art (PA), chromatography media are known in which porous matrices are modified such that they have a macroporous (un)crosslinked (hydro)gel in their pores (see, for example, U.S. Pat. Nos. 8,652,849 B2, 7,316,919 B2, 8,133,840 B2, 7,247,370 B2, EP 1 776 176 B1; referred to hereinafter as PA documents 1 to 5). According to the definition from the "Dictionary of Polymers", Katsuyoshi Nishinari, Progr. Colloid Polym. Sci. (2009) 136: 87-94, "Some Thoughts on the Definition of a Gel", and "Gels: Structures, Properties, and Functions: Fundamentals and Applications" by Katsuyoshi Nishinari (Springer Verlag Berlin Heidelberg 2009), a polymer gel consists of a three-dimensionally crosslinked network and swells in a solvent up to a certain limit, but does not dissolve itself in a good solvent for the polymer as such. According to the definition from "Römpp Online 2014", a hydrogel is a water-containing, but water-insoluble, polymer, the molecules of which are linked chemically, for example by covalent or ionic bonds, or physically, for example by entanglement of the polymer chains, to form a three-dimensional network. Owing to incorporated hydrophilic polymer components, hydrogels swell in water with a considerable increase in volume, but without losing their material cohesion.

However, these chromatography media known in the prior art also exhibit either a low flow rate or low permeability or a low dynamic binding capacity.

DETAILED DESCRIPTION

Figure 1:
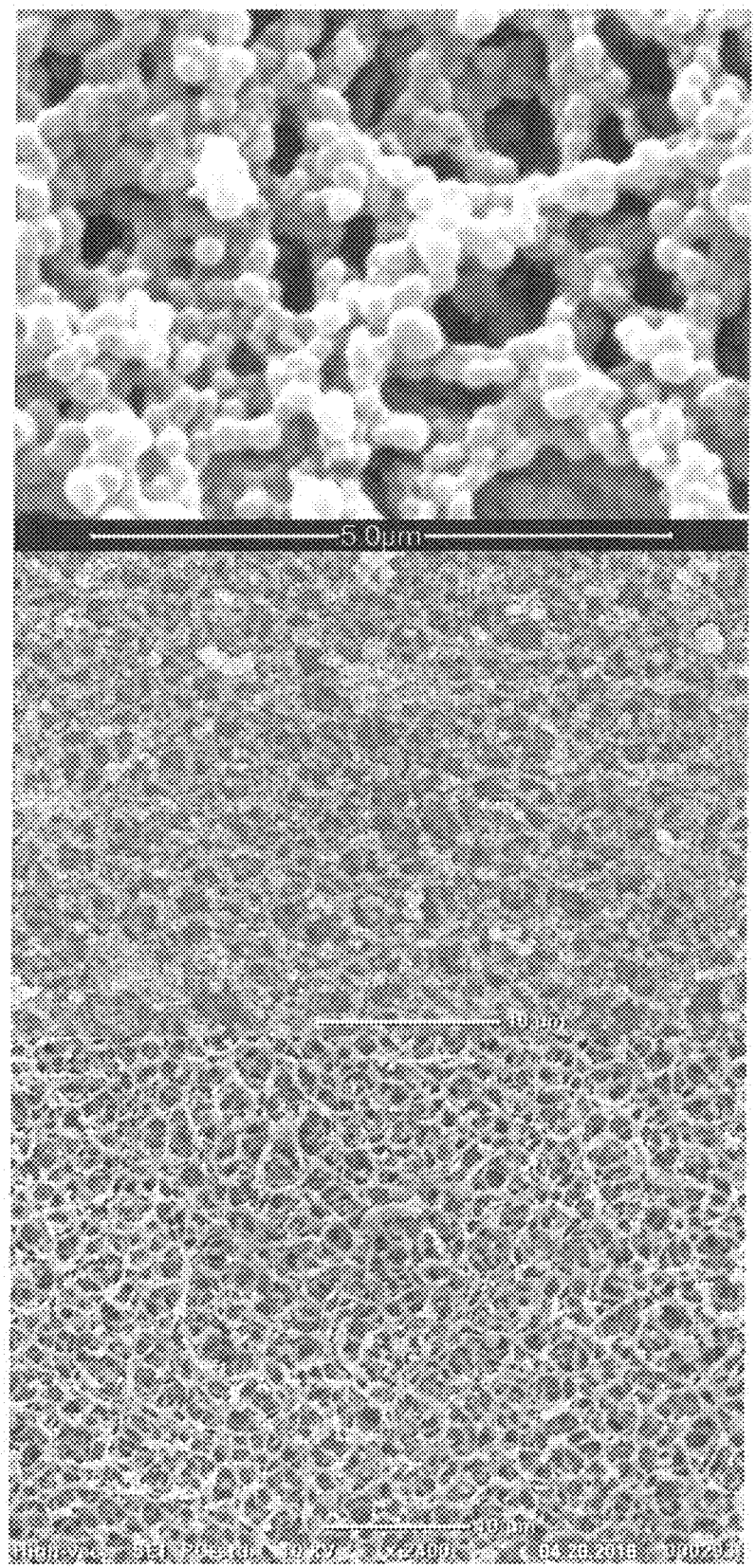
FIG. 1: SEM images of the chromatography medium according to the invention as per inventive modification 2 (top/center) and of the porous starting matrix before the modification (bottom).

It is an object of the present invention to provide a chromatography medium which both allows a high flow rate and has a high dynamic binding capacity.

This object is achieved by the embodiments of the present invention that are characterized in the claims.

In particular, what is provided according to the invention is a chromatography medium comprising
    a porous matrix; and
    nonporous microglobules,
    the nonporous microglobules being bound on the inner and outer surfaces of the porous matrix, and
    the average radius of the microglobules being not more than 30% of the average pore diameter of the porous matrix.

In the context of the present invention, the term "porous matrix" is understood to mean any porous material which can be used as stationary phase for chromatographic methods. The porous matrix of the present invention, which is referred to as "starting matrix" in the method according to the invention, is not subject to any particular restriction so long as the matrix comprises pores. The average size or the average diameter of the pores of the matrix is not subject to any particular restriction and it is possible to use, for example, a matrix having an average pore diameter of from 0.01 to 20 µm, preferably from 0.1 to 10 µm and more preferably from 0.2 to 4 µm.

The further structure of the matrix is not subject to any particular restriction. Therefore, it is possible according to the invention for the porous matrix to be, for example, a membrane (including hollow-fiber membranes), a nonwoven composed of filaments, split fibers, nanofibers or hollow fibers, short-cut fibers, or a monolith. The material of the porous matrix is not subject to any particular restriction either, and it is possible according to the invention to use, for example, membranes or nonwovens composed of cellulose hydrate/cellulose ester/cellulose acetate, cellulose nanofibers, nylon nanofibers, polyethylene terephthalate (PET), poly(oxy-1,4-phenylsulfonyl-1,4-phenyl), polyamides, polyesters, polyvinylidene fluoride (PVDF), polyethylene (PE) and/or polypropylene (PP).

What is used according to the invention is either a porous matrix which originally has groups capable of free-radical polymerization or a porous matrix in which functional groups were inserted by means of a surface modification known to a person skilled in the art. In this context, known surface modifications are, for example, a graft polymerization of monomers with functional groups ("grafting through" polymerization), activation by means of plasma treatment, electron-beam treatment, gamma irradiation, hydrolysis, aminolysis, oxidation, reduction, reaction with functional carbenes and/or nitrenes, etc. Alternatively, the porous matrix can also be used without the presence of groups capable of free-radical polymerization.

According to the invention, nonporous microglobules (microspheres) are bound on the inner and outer surfaces of the porous matrix, by physical means, for example by adhesive interactions, or by covalent means, for example by grafting, in a particularly preferred embodiment. In the context of the present invention, the term "nonporous microglobules" is substantially understood to mean spherical structures, i.e., the ratio of the minimum diameter to the maximum diameter of a microglobule is usually preferably within a range from 1:2 to 1:1. According to the invention, the average radius of the microglobules is not more than 30% of the average pore diameter of the porous matrix (i.e., the porous matrix without bound microglobules). Thus, according to the invention, the microglobules preferably have an average radius of not more than about 6 μm, more preferably of not more than 3 μm and most preferably of not more than 1.2 μm. According to the invention, the diameter or radius of a microglobule or pore is understood to mean the maximum diameter or maximum radius of the microglobule or pore. Both the diameter or radius of the pores of the porous matrix and the diameter or radius of the microglobules can be determined via scanning electron microscopy (SEM) for example.

The microglobules of the chromatography medium according to the invention are not gels or hydrogels, since they swell only very negligibly, if at all, in hydrophilic solvents, for example water and acetone. As a result, the microglobules differ significantly from the (hydro)gels of PA documents 1 to 5.

The formation of nonporous microglobules on the inner and outer surfaces of the nonporous matrix advantageously significantly increases, owing to the substantially spherical structure of the nonporous microglobules, the specific surface area of the chromatography medium in comparison with a chromatography medium which is merely constructed from a porous matrix. The significantly increased surface area of the chromatography medium of the present invention advantageously allows a higher number of chromatographically active centers, meaning that the chromatography medium according to the invention has an increased dynamic binding capacity. According to the invention, the term "chromatographically active centers" is denoted in this connection to mean functional surface groups which can selectively form bonds with certain components of fluids, the chromatographically active centers already being originally present in the microglobules or it, however, also being possible for them to be immobilized on the microglobules by means of an additional modification.

Since the average radius of the microglobules is, according to the invention, not more than 30% of the average pore diameter of the porous matrix, the pore structure of the porous matrix is preserved as far as possible, meaning that there is advantageously little impairment of the permeability of the chromatography medium according to the invention in comparison with a chromatography medium which is merely constructed from a porous matrix. Consequently, the chromatography medium according to the invention advantageously allows a high flow rate (permeability) and has moreover a high dynamic binding capacity. According to a preferred embodiment of the present invention, the permeability of the chromatography medium is at least 40% of the permeability of the starting matrix (i.e., the porous matrix of the chromatography medium without bound microglobules), preferably at least 50%, more preferably at least 60% and most preferably at least 70%.

Moreover, the microglobules make it possible to optimize the pore size of the porous matrix with respect to affinity-chromatography use, i.e., it is possible in particular to optimize those pores of the porous matrix which would have an excessively large pore size in the absence of the nonporous microglobules, meaning that a target molecule would convectively pass through said pores in the chromatography process without exhibiting interactions with the surface while doing so.

According to the invention, the microglobules are nonporous, i.e., they do not have any pores. Owing to the nonporous microglobules, there are advantageously no pores which are reachable only by diffusion. This minimizes a dependency of the dynamic binding capacity on the residence time, since this then solely depends on the diffusion of the chromatography target molecule toward the chromatographically active center. Moreover, this increases the accessibility to the chromatographically active centers in a dynamic separation process, meaning that it is possible in particular to minimize the consumption of chromatographically active centers introduced later into the chromatography medium, such as (affinity) ligands for example, since the ligands are not immobilized in pores inaccessible for the chromatography target molecule during the immobilization (incorporation) process.

The microglobules of the chromatography medium according to the invention are not subject to any particular restriction so long as their average radius is not more than 30% of the average pore diameter of the porous (starting) matrix. The material of the microglobules is not subject to any particular restriction either. According to a preferred embodiment, the nonporous microglobules are substantially spherical oligomers and/or polymers, especially oligomers and/or polymers which are constructed from at least one monomer selected from the group consisting of glycidyl (meth)acrylate, substituted or unsubstituted alkyl (meth)acrylates and their derivatives (particularly preferably methyl (meth)acrylate, butyl (meth)acrylate or hydroxyethyl (meth)acrylate), styrene and its derivatives (particularly preferably chloromethylstyrene or 4-acetoxystyrene), 2-vinyl-4,4-dimethylazlactone, substituted or unsubstituted N-alkyl(meth)acrylamides and their derivatives and substituted or unsubstituted N-N'-dialkyl(meth)acrylamides and their derivatives, since they are synthetically obtainable in a suitable manner as described below. According to a preferred embodiment, the at least one monomer has an epoxy function, since further chromatographically active centers, such as (affinity) ligands for example, can be introduced synthetically in an easily obtainable manner via said function and/or the microglobules can be bound to the porous matrix in a simple manner via said function. According to a further embodiment of the present invention, the microglobules are merely constructed from a single monomer.

According to a preferred embodiment of the present invention, the nonporous microglobules are bound on the inner and outer surfaces of the porous matrix in a monolayer. By contrast, if the nonporous microglobules are bound on the porous matrix in multilayers, there is the risk that the pores of the porous matrix become clogged, and this can adversely affect the permeability of the chromatography medium according to the invention.

According to a preferred embodiment of the present invention, the degree of grafting P of the chromatography medium is from 25% to 40%. The degree of grafting P is given by:

$$P = \frac{m_m - m_0}{m_0} * 100\%$$

where $m_m$ is the mass of the chromatography medium according to the invention and $m_0$ is the mass of the porous matrix (without bound microglobules). If the degree of grafting P is more than 40%, the permeability of the chromatography medium may decline. By contrast, if the degree of grafting is less than 25%, the surface area of the chromatography medium may be enlarged only to a relatively slight extent in comparison with the porous (starting) matrix.

According to a preferred embodiment of the present invention, the relative degree of grafting $P_{rel}$ of the chromatography medium is at most 0.25 g/cm³. The relative degree of grafting $P_{rel}$ is given by:

$$P_{rel} = \frac{P * \rho}{Por}$$

where P is the above-defined degree of grafting of the chromatography medium in %, $\rho$ is the density of the porous matrix (without microglobules) in g/cm³, and Por is the porosity of the porous matrix (without microglobules) in %. If the relative degree of grafting of the chromatography medium is, as in PA documents 1 to 5, more than 0.25 g/cm³, the permeability of the chromatography medium may decline.

According to one embodiment of the present invention, the nonporous microglobules comprise additional chromatographically active centers or ligands which are bound to the microglobules or immobilized thereon. The additional chromatographically active centers or ligands are capable of selectively forming bonds with certain components of fluids in chromatography processes.

By way of example, chromatographically active centers or ligands that can be mentioned are ion exchangers, chelating agents and heavy metal chelates, thiophilic, hydrophobic ligands of various chain lengths and configurations, reversed-phase systems, dye ligands, affinity ligands, amino acids, coenzymes, cofactors and analogs thereof, substrates and analogs thereof, endocrine and exocrine substances, such as hormones and substances with hormone-like action, effectors and analogs thereof, enzyme substrates, enzyme inhibitors and analogs thereof, fatty acids, fatty acid derivatives, conjugated fatty acids and analogs thereof, nucleic acids, such as DNA, RNA and analogs and derivatives thereof (single-stranded, double-stranded and/or multi-stranded), and also peptide nucleic acids and derivatives thereof, viruses, virus particles, monomers and analogs and derivatives thereof, oligomers to polymers and analogs and derivatives thereof, high-molecular-weight carbohydrates, which may be linear or branched, unsubstituted or substituted, polymeric glycoconjugates, such as heparin, amylose, cellulose, chitin, chitosan and monomers and oligomers thereof and derivatives and analogs thereof, lignin and derivatives and analogs thereof, other biological/chemical ligands, such as oligopeptides and polypeptides, for example proteins and their oligomers, multimers, subunits and also parts thereof, especially lectins, antibodies, fusion proteins, haptens, enzymes and subunits and also parts thereof, structural proteins, receptors and effectors and also parts thereof, additionally xenobiotics, pharmaceuticals and active pharmaceutical ingredients, alkaloids, antibiotics, biomimetics, etc. According to one embodiment of the present invention, the additional chromatographically active centers or ligands are selected from the group consisting of anionic and cationic groups, hydrophobic groups, affinity ligands, metal chelates and reactive epoxide, aldehyde, azlactone, N-hydroxysuccinimide and/or carbodiimide groups. According to a particularly preferred embodiment of the present invention, the additional chromatographically active centers or ligands are protein A or protein B.

A further aspect of the present invention concerns a method for preparing the chromatography medium according to the invention, comprising providing a porous starting matrix;

providing a polymerization solution comprising at least one monomer, a bi-, tri- or multifunctional crosslinker, a polymerization initiator and a solvent or solvent mixture, the at least one monomer, the bi-, tri- or multifunctional crosslinker and the polymerization initiator being completely soluble in the solvent or solvent mixture; and initiating the polymerization in the polymerization solution in the presence of the porous starting matrix to form nonporous microglobules, the nonporous microglobules being insoluble in the solvent or solvent mixture and being bound to the inner and outer surfaces of the porous starting matrix;

the average radius of the microglobules being not more than 30% of the average pore diameter of the porous starting matrix.

All the above remarks concerning the chromatography medium according to the invention also apply to the method according to the invention for preparing the chromatography medium according to the invention.

In the first step of the method according to the invention, a porous starting matrix is provided. The porous starting matrix is not subject to any particular restriction and it is possible to use, for example, the porous matrices described above for the chromatography medium according to the invention. Such porous starting matrices are commercially available or can be prepared by methods known to a person skilled in the art.

In the second step of the method according to the invention, a polymerization solution is provided, comprising at least one monomer, a bi-, tri- or multifunctional crosslinker, a polymerization initiator and a solvent or solvent mixture, the at least one monomer, the bi-, tri- or multifunctional crosslinker and the polymerization initiator being completely soluble in the solvent or solvent mixture.

According to the invention, it is possible to use either a single monomer or a mixture of two or more different monomers. The at least one monomer is not subject to any particular restriction so long as it is completely soluble in the solvent or solvent mixture used. According to a preferred embodiment, the at least one monomer is selected from the group consisting of glycidyl (meth)acrylate, substituted or unsubstituted alkyl (meth)acrylates and their derivatives (particularly preferably methyl (meth)acrylate, hydroxyethyl (meth)acrylate or butyl (meth)acrylate), styrene and its derivatives (particularly preferably chloromethylstyrene or 4-acetoxystyrene), 2-vinyl-4,4-dimethylazlactone, substituted or unsubstituted N-alkyl(meth)acrylamides and their derivatives and substituted or unsubstituted N,N'-dialkyl (meth)acrylamides and their derivatives. According to a preferred embodiment, the at least one monomer has an epoxy function, since further chromatographically active centers, such as (affinity) ligands for example, can be introduced synthetically in an easily obtainable manner via said function and/or the microglobules can be bound to the porous matrix in a simple manner via said function.

Furthermore, the polymerization solution comprises a bi-, tri- or multifunctional crosslinker in the method according to the invention. According to the invention, the term "crosslinker" is understood to mean a reagent which is capable of crosslinking the resultant microglobules to the inner and outer surfaces of the porous starting matrix and is in particular capable of crosslinking the oligomers or polymers to one another to yield the nonporous microglobular structure according to the invention. The crosslinker in the method according to the invention is not subject to any particular restriction so long as it is completely soluble in the solvent or solvent mixture used and is bi-, tri- or multifunctional, i.e., has two, three or more functional groups via which the three-dimensional network to be formed is linked. According to the invention, it is possible to use either a single crosslinker or a mixture of two or more crosslinkers. According to a preferred embodiment, the bi-, tri- or multifunctional crosslinker is selected from the group consisting of ethylene glycol dimethacrylate, trimethylpropane trimethacrylate, divinylbenzene and N-N-methylenebisacrylamide.

Furthermore, the polymerization solution comprises a polymerization initiator in the method according to the invention. According to the invention, the term "polymerization initiator" is understood to mean a reagent which is capable of triggering a free-radical polymerization, for example by UV irradiation or by thermal energy input. The polymerization initiator in the method according to the invention is not subject to any particular restriction so long as it is completely soluble in the solvent or solvent mixture used. According to the invention, it is possible to use either a single polymerization initiator or a mixture of two or more polymerization initiators. According to a preferred embodiment, the polymerization initiator is selected from the group consisting of 2-hydroxy-4-(2-hydroxyethoxy)-2-methylpropiophenone, azobis(isobutyronitrile), 4,4-azobis(4-cyanovaleric acid), 1,1'-azobis(cyclohexanecarbonitrile), benzoyl peroxide, 2,2-bis(tert-butylperoxy)butane, 1,1-bis(tert-butylperoxy)cyclohexane, tert-butyl hydroperoxide, tert-butyl peroxyisopropyl carbonate, cyclohexanone peroxide and 2,4-pentanedione peroxide.

In the third step of the method according to the invention, a polymerization in the polymerization solution in the presence of the porous starting matrix is initiated to form nonporous microglobules, the nonporous microglobules being insoluble in the solvent or solvent mixture and being bound to the inner and outer surfaces of the porous starting matrix. The initiation of the polymerization is not subject to any particular restriction and can, for example, be done by UV irradiation and/or by thermal means.

In the polymerization, nonporous microglobules are formed, with the nonporous microglobules being bound to the inner and outer surfaces of the porous starting matrix by physical means (e.g., by adhesion) or by covalent means (e.g., by graft polymerization). The nonporous microglobules are insoluble in the solvent or solvent mixture used, i.e., there is no dissolution within a detectable range.

The solvent or solvent mixture in the second and third step of the method according to the invention is not subject to any particular restriction so long as the at least one monomer, the bi-, tri- or multifunctional crosslinker and the polymerization initiator are completely soluble therein, i.e., there is a homogeneous polymerization solution, whereas the microglobules arising in the third step are completely insoluble in the solvent or solvent mixture. Therefore, according to a preferred embodiment, use is made of a solvent or solvent mixture selected from the group consisting of cyclohexanol/dodecan-1-ol, octan-2-one, n-butyl acetate, p-xylene, toluene, ethyl acetate, benzonitrile, cyclohexanone, dodecan-1-ol, acetonitrile/ethanol/water, decan-1-ol and isopropanol/decan-1-ol.

The average radius of the microglobules arising in the third step of the method according to the invention is not more than 30% of the average pore diameter of the porous starting matrix (i.e., the porous starting matrix without microglobules). This is achieved by the nonporous microglobules arising during the polymerization on the basis of the rapid decomposition of the polymerization initiator, which reacts rapidly with the at least one monomer to form oligomers and polymers. The resultant rapid macroscopically observable phase separation, preferably within not more than 30 seconds, in the solvent or solvent mixture in which the growing polymer chains do not dissolve leads to the formation of the nonporous microglobules. As a result of interactions with the surface due to the ratio used of monomer and crosslinker to the total volume of the reaction solution and as a result of the very short reaction time, the nonporous microglobules form only on the inner and outer surfaces of the porous starting matrix and do not form a cohesive network which would fill the pore spaces of the porous starting matrix and thus form its own porosity. As a result, the pore structure of the porous starting matrix is preserved as far as possible, meaning that an impairment of the permeability of the chromatography medium, as would be the case for a complete filling of the pores as per PA documents 1 to 5, can be distinctly reduced.

To achieve the above-described formation of the globules, preference is given to using a polymerization solution in which the total volume of monomer and crosslinker, based on the total volume of the polymerization solution, is not more than 20% by volume. Moreover, the total volume of the crosslinker, based on the total volume of the polymerization solution, is preferably not more than 6% by volume. In addition, the concentration of the polymerization initiator in the polymerization solution is preferably from 1 to 3% by weight. By coordinating the aforementioned preferred conditions and constituents of the polymerization solution, it is possible to ensure that the macroscopically observable phase separation occurs after not more than 30 seconds, preferably after not more than 20 seconds, meaning that microglobules physically or covalently bound to the inner and outer surfaces of the porous starting matrix arise, the average radius of which is not more than 30% of the average pore diameter of the porous starting matrix. According to the invention, "macroscopically observable phase separation" is understood to mean the attainment of a heterogenous, biphasic or multiphasic state of the previously homogeneous polymerization solution present in a single phase. There is very little agglomeration of the microglobular structure during the polymerization, i.e., there is only very little crosslinking of the microglobules with one another while they arise, meaning that filling of the pores of the porous starting matrix is prevented as far as possible in contrast to the chromatography media known from PA documents 1 to 5.

Owing to the nonporous microglobules on the inner and outer surfaces of the porous matrix of the chromatography medium according to the invention, the specific surface area of the chromatography medium is advantageously significantly increased in comparison with a chromatography medium which is merely constructed from a porous matrix. This advantageously allows a higher number of chromatographically active centers, meaning that the chromatography medium according to the invention has an increased dynamic binding capacity. At the same time, the pore structure of the porous matrix is preserved as far as possible, meaning that there is advantageously little impairment of the permeability of the chromatography medium according to the invention in comparison with a chromatography medium which is merely constructed from a porous matrix. Consequently, the chromatography medium according to the invention advantageously allows a high flow rate and has moreover a high dynamic binding capacity. Moreover, the microglobules advantageously make it possible to optimize the pore size of the porous matrix with respect to affinity-chromatography use, i.e., it is possible in particular to optimize those pores of the porous matrix which would have an excessively large pore size in the absence of the nonporous microglobules, meaning that a target molecule would convectively pass through said pores in the chromatography process without exhibiting interactions with the surface while doing so. Owing to the nonporous microglobules, there are advantageously no pores which are reachable only by diffusion. This advantageously minimizes a dependence of the dynamic binding capacity on the residence time. Moreover, this increases the accessibility to the chromatographically active centers in a dynamic separation process, meaning that it is possible in particular to minimize the consumption of chromatographically active centers introduced later into the chromatography medium, such as (affinity) ligands for example, since the ligands are not immobilized in pores inaccessible for the chromatography target molecule while they are immobilized (introduced). The chromatography medium according to the invention is therefore outstandingly suitable for use in affinity chromatography, especially for protein A or B affinity chromatography.

The present invention will be more particularly elucidated on the basis of the following examples which have no limiting effect.

EXAMPLES

Porous Starting Matrices:

The porous matrices used as starting matrices in the method according to the invention with a pore size of from 0.01 to 20 µm, preferably 0.1 to 10 µm and more preferably from 0.2 to 4 µm were prepared by customary preparation methods known to a person skilled in the art. Pore size was determined by carrying out a capillary flow porometry test. Details for the determination can be gathered from the corresponding operating instructions (Capillary Flow Porometer 6.0, CAPWIN Software System, Porous Materials Inc.).

Example 1

Pretreatment of the Surfaces

Pretreatment of the cellulose starting material to generate unsaturated functionalities on the surface of the porous starting matrix

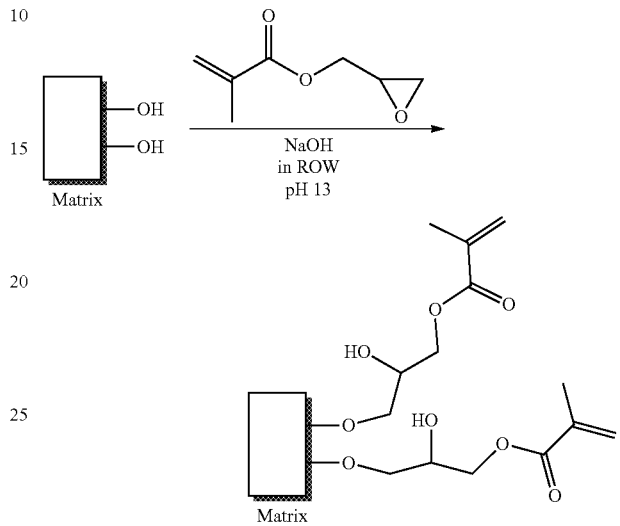

In a typical reaction, the starting material, regenerated stabilized cellulose, was impregnated overnight in a 20% by weight solution of glycidyl methacrylate in water that was adjusted to pH 13 using sodium hydroxide, and then rinsed with reverse-osmosis water ("RO water") for 15 minutes. Thereafter, the treated membranes were dried at 80° C. for 30 minutes.

Example 2

Generation of the Graft Polymer on the Treated Surface

For a typical polymerization solution, what were weighed out or measured and treated in an ultrasonic bath for 30 minutes until complete dissolution were, for example, 1.7 mL (1.82 g; 12.79 mmol; 0.10 Eq.) of glycidyl methacrylate (monomer), 0.16 g (0.71 mmol; 7·10$^{-3}$ Eq.) of 2-hydroxy-4-(2-hydroxyethoxy)-2-methylpropiophenone (polymerization initiator), 0.33 mL (0.347 g; 1.75 mmol; 0.013 Eq.) of ethylene glycol dimethacrylate (crosslinker), 0.34 mL (0.28 g; 1.78 mmol; 0.014 Eq.) of 1-decanol and 13.36 mL (12.85 g; 128.32 mmol; 1.00 Eq.) of cyclohexanol (solvent mixture). Thereafter, the samples wetted with polymerization solution were irradiated with UV light (ultraviolet light; 254 nm, 40 W) (5 minutes) under inert conditions ($N_2$ atmosphere). For the UV-initiated, conventional, free-radical polymerization which takes place here, use was made of a BLX-E254 BIO-Link UV crosslinker from the manufacturer LLG. The polymerized membranes were then rinsed under running RO water for 10 minutes and then shaken in acetone for 20 minutes and air-dried.

Schematic depiction of the polymerization mechanism.
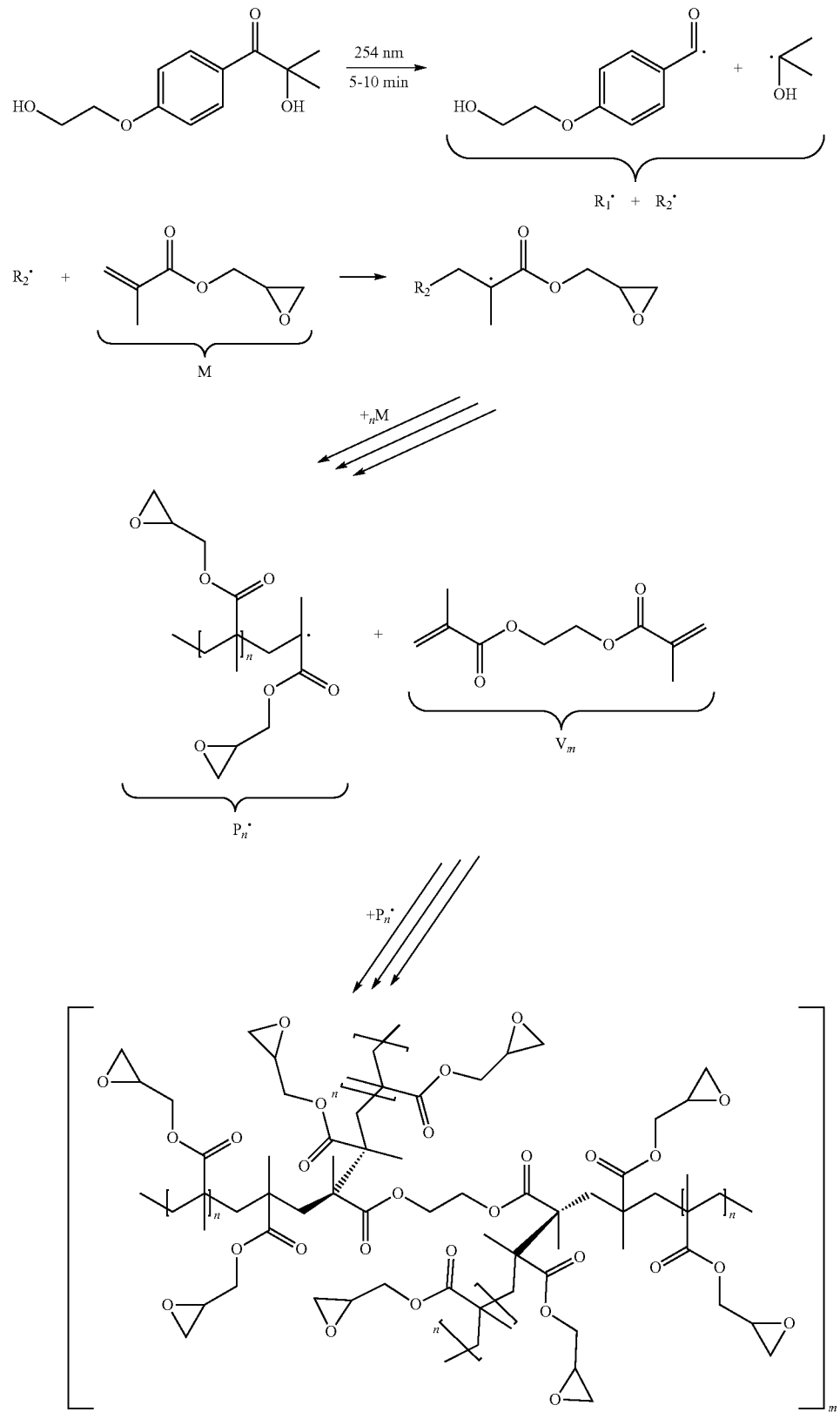

The following specific exemplary embodiments indicating the chemicals used and the amount used in each case, in % by volume and % by weight, were carried out:

|  | Initiator [% by weight] | Crosslinker [% by volume] | Monomer [% by volume] | Solvent 1 [% by volume] | Solvent 2 [% by volume] |
|---|---|---|---|---|---|
| Inventive modification 1 | 2-Hydroxy-4-(2-hydroxy-ethoxy)-2-methylpropio-phenone/1 | Ethylenedi-methacrylate/4 | Glycidyl methacrylate/16 | 1-Decanol/9 | Cyclo-hexanol/70 |
| Inventive modification 2 | 2-Hydroxy-4-(2-hydroxy-ethoxy)-2-methylpropio-phenone/1 | Ethylenedi-methacrylate/6 | Glycidyl methacrylate/14 | 1-Decanol/3 | Cyclo-hexanol/76 |
| Inventive modification 3 | 2-Hydroxy-4-(2-hydroxy-ethoxy)-2-methylpropio-phenone/1 | Ethylenedi-methacrylate/5 | Glycidyl methacrylate/15 | 1-Decanol/10 | Cyclo-hexanol/69 |
| Inventive modification 4 | 2-Hydroxy-4-(2-hydroxy-ethoxy)-2-methylpropio-phenone/1 | Ethylenedi-methacrylate/2 | Glycidyl methacrylate/18 | 1-Decanol/15 | Cyclo-hexanol/64 |

FIG. 1 shows SEM images of the chromatography medium according to the invention due to inventive modification 2 (top/center) and of the porous starting matrix before the modification (bottom). FIG. 1 clearly shows that the microglobules are merely grafted onto the surfaces of the starting matrix and the actual pore structure of the starting matrix is virtually preserved. Moreover, it is clearly evident that the microglobules themselves do not exhibit porosity.

Figure 2:
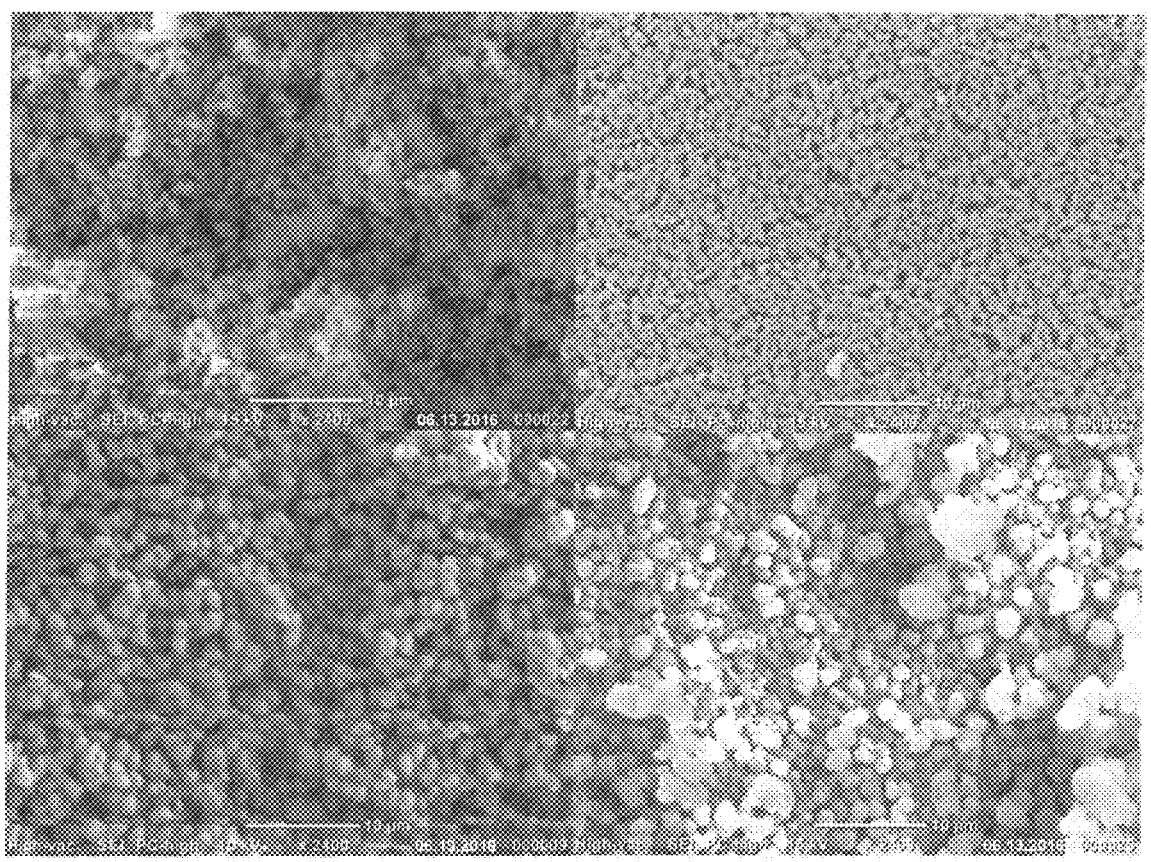
FIG. 2: SEM images of chromatography media as per the modification protocols of PA documents 2 (top left), 5 (top right), 1 (bottom left) and 4 (bottom right).

FIG. 2 by contrast shows SEM images of chromatography media which, with the same starting matrix, were modified in accordance with the modification protocols of PA documents 2 (top left), 5 (top right), 1 (bottom left) and 4 (bottom right). Under these modification conditions, a differentiated microglobular structure does not appear and it can be readily recognized that the pores of the porous starting matrices are completely filled and the globular structures, if present at all, are very highly agglomerated, meaning that the effective surface area is greatly lowered and what arises is an additional monomer-generated porosity in the pores of the starting matrices.

Example 3

Determination of the Permeability of the Chromatography Media

Using a round puncher, 47 mm circular blanks were punched out from the chromatography media as per Example 2. The 47 mm punches obtained were wetted with reverse-osmosis water and were rinsed under running reverse-osmosis water for 5 minutes. Each punch was fitted into a top-feed filtration housing, Sartorius model 16249.

Each measurement was done at 20-25° C. and 0.10 bar positive pressure. What was measured was the time required by 100.0 g of medium in order to flow through the chromatography medium. The specified unit of the flow rate thus ascertained is ml/cm²×min×bar. The media used are both reverse-osmosis water and phosphate-buffered saline solution having a pH of 7.5. After flow-rate determination, it was possible to use the punches for further analyses.

Figure 3:
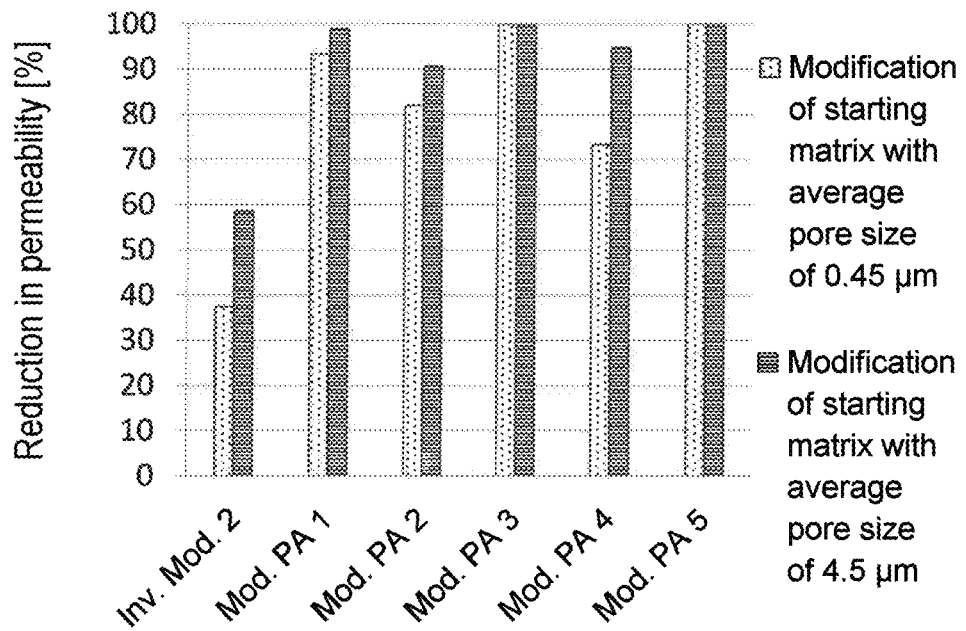
FIG. 3: Reduction in permeability as per Example 3.

FIG. 3 shows that, as a result of inventive modification 2 ("Inv. Mod. 2") of the porous starting matrix via formation of microglobules on the inner and outer surfaces of the starting matrix, the permeability is at least 40% of the permeability of the unmodified starting matrix. By contrast, if the starting matrix is modified in accordance with the modification protocols of PA documents 1 to 5 ("Mod. PA 1 to 5"), the permeability of the modified chromatography medium is not more than 26% of the permeability of the unmodified starting matrix, in most cases even markedly below 20% of the starting permeability.

Example 4

Immobilization of Proteins

Proteins (ligands) were immobilized by converting the epoxide functionalities of the microglobules of the chromatography media according to the invention to aldehyde functionalities. It was possible for the protein (ligand) to be directly immobilized thereon. To this end, the chromatography medium modified according to the invention was placed in a 3% (% by weight) sodium metaperiodate solution in RO water for 30 min and subsequently rinsed under running RO water for 10 minutes and dried of acetone in air. Thereafter, the chromatography media thus prepared were placed for 2 h in a 2.5% (% by weight) sodium cyanoborohydride solution in potassium hydrogenphosphate buffer (pH 8), to which 4.958 µL/cm² of recombinant protein solution (1 mL≙50.4 mg of protein) were added in order to achieve a concentration of 7.2 mg/mL. Thereafter, the chromatography media were rinsed again with RO water and placed in a 0.01% (% by weight) sodium borohydride solution in RO water for 10 min. Thereafter, the chromatography media were washed with 1× PBS buffer (phosphate-buffered saline solution) and subsequently stored in a 20% ethanol/PBS solution.

Example 5

Determination of the Binding Capacity for Immunoglobulin G

The binding of immunoglobulin G (IgG) was determined by using an appropriate protein solution (1 mg/mL) in PBS buffer (pH=7.5). 3 layers of membrane, modified according to the invention as per Example 2 and functionalized with protein A as per Example 4, were clamped into a membrane holder. The membrane stack had a membrane area of 15 cm², an inflow area of 5 cm² and a bed height (thickness of the membrane stack) of 500 μm in the membrane holder. The membranes in the membrane holder were flooded with 1× PBS buffer (pH=7.5) in order to displace the air and then connected to an Äkta Explorer 100 FPLC system from General Electric Health Care.

Afterwards, the membranes, or the membrane stack, were analyzed with respect to IgG binding using a test program comprising four steps. The four steps of the test program are specified below:
1. equilibration of the membrane with 25 mL of 1× PBS buffer (pH=7.5),
2. loading of the membrane with 50 mL of IgG solution,
3. washing with 20 mL of 1× PBS buffer (pH=7.5), and
4. elution with 0.1% glycine solution (pH=3.5).

All the steps were carried out at a flow rate of 5 membrane volumes/min. In all the steps, the absorption at 280 nm was measured in the detector after the membrane unit.

Figure 4:
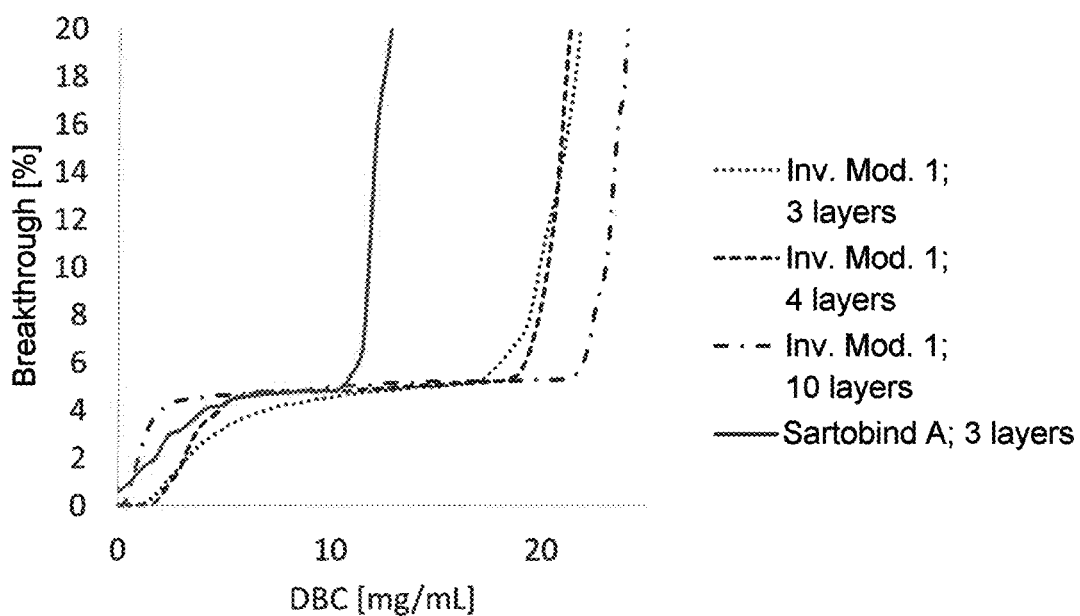
FIG. 4: Breakthrough curves of chromatography media according to the invention and of Sartobind A, plotted as percentage breakthrough against dynamic binding capacity DBC.

FIG. 4 shows the breakthrough curves of the chromatography media prepared according to the invention as per inventive modification 1, plotted as percentage breakthrough against dynamic binding capacity DBC. Plotted as reference is the breakthrough curve of a commercially available protein A membrane adsorber (Sartobind A). FIG. 4 clearly shows that the specific surface area of the chromatography medium according to the invention is significantly increased as a result of the inventive modification, i.e., as a result of the formation of microglobules, and this advantageously leads to a distinctly higher dynamic binding capacity.

Example 6

Determination of the Specific Surface Area of the Modified Membranes as per Example 2

The surface-area determinations performed were carried out with the aid of a Gemini V from micromeritics. The samples to be measured were weighed beforehand and placed into the sample chamber. It was subsequently entirely heated at 70° C. and 2 mbar (negative pressure generated by a VacPrep 061 from micromeritics) for 2 h. Thereafter, the sample chamber was flushed with nitrogen and entirely heated again at 70° C. and 2 mbar for 1 h. For the actual measurement, nitrogen was guided across the material to be analyzed. On the basis of cooling by liquid nitrogen (−196° C.), it was possible using a standard-pressure measuring instrument to determine, below the saturation vapor pressure of the nitrogen, the adsorbed amount (adsorption). Subsequent reduction of the pressure within the apparatus detached a portion of the adsorbed gas amount from the surface (desorption). As a result, it was possible to ascertain an adsorption/desorption isotherm. Within the relative pressure range from 0.05 mbar to 0.3 mbar, the amount of adsorbed or released gas that is measured in this connection is proportional to the surface area. The results were outputted directly in m²/g.

Figure 5:
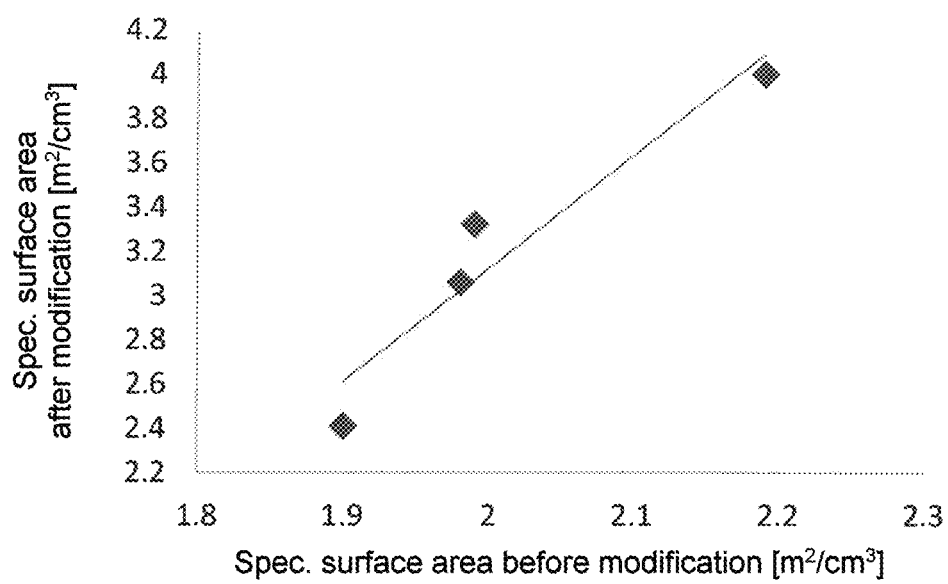
FIG. 5: Plot of the specific surface areas after inventive modification and before modification.
Figure 6:
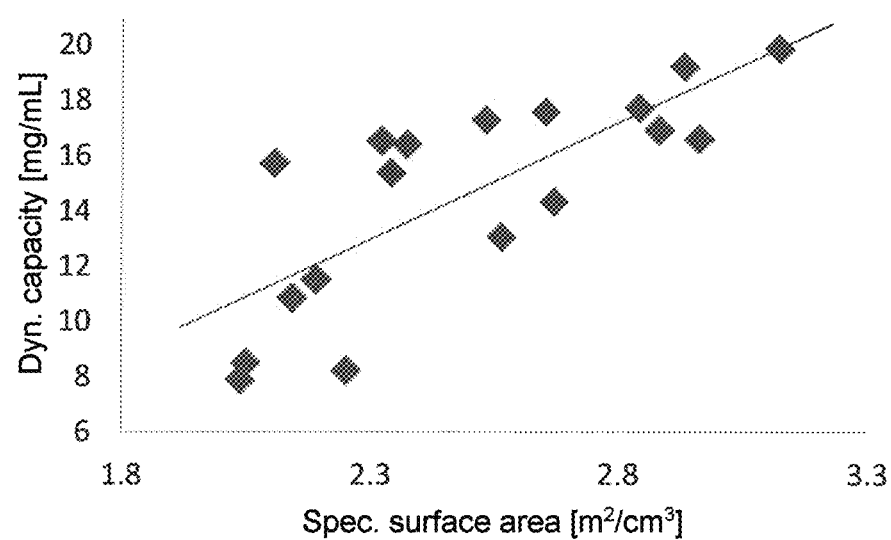
FIG. 6: Plot of the dynamic capacity of chromatography media according to the invention against their specific surface area.

FIG. 5 shows a plot of the specific surface areas after inventive modification and before modification (i.e., the porous starting matrices without microglobules). Regardless of the specific surface area of the starting matrix, the specific surface area of the chromatography medium according to the invention is, as a result of formation of the microglobular structure, always greater than before the modification. As is evident from FIG. 6, under otherwise identical conditions, the inventive modification advantageously leads to increased dynamic binding capacities of IgG on protein A membrane adsorbers (immobilization as per Example 4).

Example 7

Determination of the Pore Sizes of the Chromatography Media According to the Invention and Determination of the Porosities by Means of Inverse Size-Exclusion Chromatography (ISEC)

Pore size was determined by carrying out a capillary flow porometry test. Details can be gathered from the corresponding operating instructions (Capillary Flow Porometer 6.0, CAPWIN Software System, Porous Materials Inc.).

All porosity-determination experiments were carried out on a Standard Agilent LC System (Agilent Technologies), consisting of a quaternary pump with degasser, a temperature-adjusted autosampler, a diode array detector (DAD) and a refractive index (RI) detector. Acetone tracer signals were recorded using the DAD at a wavelength of 280 nm. Pullulan tracer signals were tracked using the RI detector. For all recorded signals, the first and second statistical moment was measured and was calculated as proposed by Haynes and Sarma et al. (AIChE Journal, Volume 19, No. 5, pp. 1043-1046). The values thus obtained were moreover corrected in order to take into account the influence of the HPLC system:

$$\mu_{p,obs} = \frac{\int_0^\infty C_i(L,t) \cdot t \cdot dt}{\int_0^\infty C_i(L,t) \cdot dt}$$

$$\sigma_{p,obs}^2 = \frac{\int_0^\infty C_i(L,t) \cdot (t - \mu_{p,obs})^2 \cdot dt}{\int_0^\infty C_i(L,t) \cdot dt}$$

$$\mu_p = \mu_{p,obs} - \mu_{HPLC}$$

$$\sigma_p^2 = \sigma_{p,obs}^2 - \sigma_{HPLC}^2$$

where $\mu_p$ and $\sigma_p^2$ stand for the first and second statistical moment of the tracer signal, $\mu_{p,obs}$ and $\sigma_{p,obs}^2$ relate to the entire system, whereas $\mu_{HPLC}$ and $\sigma_{HPLC}^2$ only describe the influence of the HPLC system. $C_i(L,t)$ describes the concentration of tracer substance i at the detector at time point t.

To determine the porosity of the particular chromatographic medium as a function of the molecular size of the tracer, use was made of pullulan molecules with different molar masses as tracer substances. Their hydrodynamic radius was calculated on the basis of the molar mass, as proposed by Segre et al. (Biomacromolecules 2003, 4, 1843-1847). The accessible volume fraction in the chromatographic bed as a function of the molecular size was calculated as follows:

$$\varepsilon = \frac{V}{F/\mu_p}$$

where ε stands for the accessible volume fraction (porosity), V stands for the column volume and F stands for the volumetric flow rate.

Figure 7:
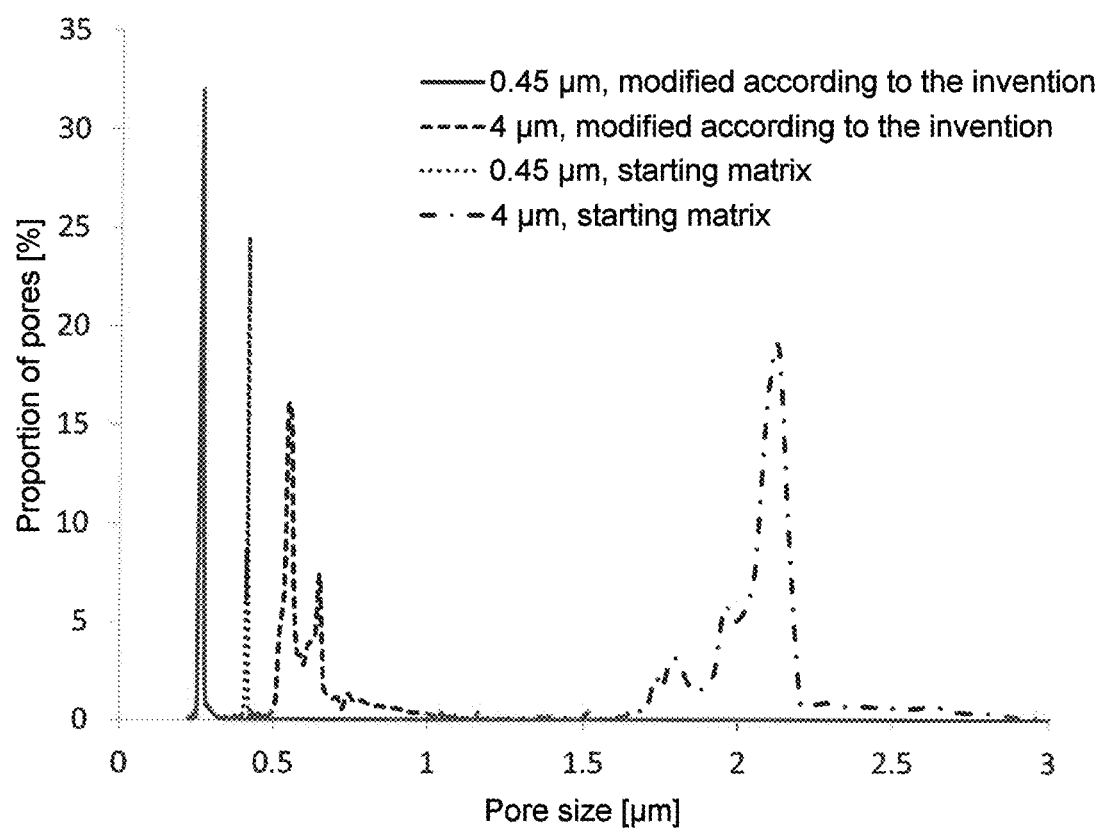
FIG. 7: Pore-size distribution of chromatography media according to the invention and of unmodified starting matrices (top); plot of porosity of chromatography media according to the invention against the hydrodynamic diameter of tracer molecules (bottom).

FIG. 7 shows the pore-size distribution of chromatography media according to the invention (as per inventive modification 1) compared to the porous starting matrices used (top) and a plot of porosity against the hydrodynamic diameter of the tracer molecule, ascertained via ISEC, for starting matrices and a chromatography medium modified according to the invention (bottom). As is evident from FIG. 7, it is possible according to the invention to adjust the pore size of the starting matrix depending on the application, and, after inventive modification, the chromatography media have in any case a smaller pore size than the starting matrices. This merely comes about as a result of a size-reduction of the pre-existing pores of the starting matrices due to grafting of the nonporous microglobules. Moreover, FIG. 7 shows via comparative measurements of various starting matrices with the same modification that a porosity of the microglobules can be ruled out. If the microglobules were namely porous or if clogging of the pores of the starting matrix with a crosslinked macroporous gel were to arise, an overlap of the pore distribution would have to arise despite the various starting materials with the same modification, but this is not the case.

Example 8

Determination of the Degree of Swelling and Grafting of Chromatography Media According to the Invention The degree of swelling describes the relative increase in volume of the polymer membrane upon swelling in solvents. For practical reasons, it was determined in PBS buffer for protein A affinity adsorbers. To this end, what were determined were, firstly, the volumes of the chromatography media in the dry state ($V_0$) and, secondly, in the wet state ($V_Q$). To rule out measurement inaccuracies due to water content as far as possible, the measurement of dry volume was performed after drying at 80° C. (30 min) in a drying cabinet. The degree of swelling Q was determined via the following formula:

$$Q[\%] = \frac{V_Q - V_0}{V_0} \cdot 100\%$$

The following table shows the results from swelling and flow-rate measurements with water and acetone as per Example 3 and Example 8, measured on a chromatography medium as per inventive modification 1 and on the porous starting matrix (cellulose membrane) without modification:

| | Cellulose membrane | Cellulose membrane, modified according to the invention |
|---|---|---|
| Swelling, $H_2O$ [%] | 22.15 ± 1.1% | 5.97 ± 1.1% |
| Swelling, acetone [%] | 4.52 ± 1.1% | 6.18 ± 1.1% |
| Permeability, $H_2O$ [mD] | / | 2.65 ± 0.08% |
| Permeability, acetone [mD] | / | 2.70 ± 0.12% |

Swelling in water as hydrophilic solvent, which is exhibited by the starting materials owing to their hydrophilic structure, is prevented as far as possible by the grafted microglobules, whereas what takes place in acetone as aprotic solvent is only a very low swelling mainly caused by the starting matrix. Permeability, too, shows no significant difference in the two solvents. This additionally rules out swelling. By definition, the grafted microglobules thus cannot be considered to be a polymeric gel/hydrogel, in contrast to the polymers from PA documents 1 to 5.

The degree of grafting describes the relative increase in mass of the starting matrix after the modification. To this end, what were determined were, firstly, the masses of the starting matrix before the modification ($m_0$) and, secondly, after the modification ($m_m$). To rule out measurement inaccuracies due to water content as far as possible, the measurement of mass was performed after drying at 80° C. (30 min) in a drying cabinet. The degree of grafting P was calculated via the following formula:

$$P[\%] = \frac{m_m - m_0}{m_0} \cdot 100\%$$

Figure 8:
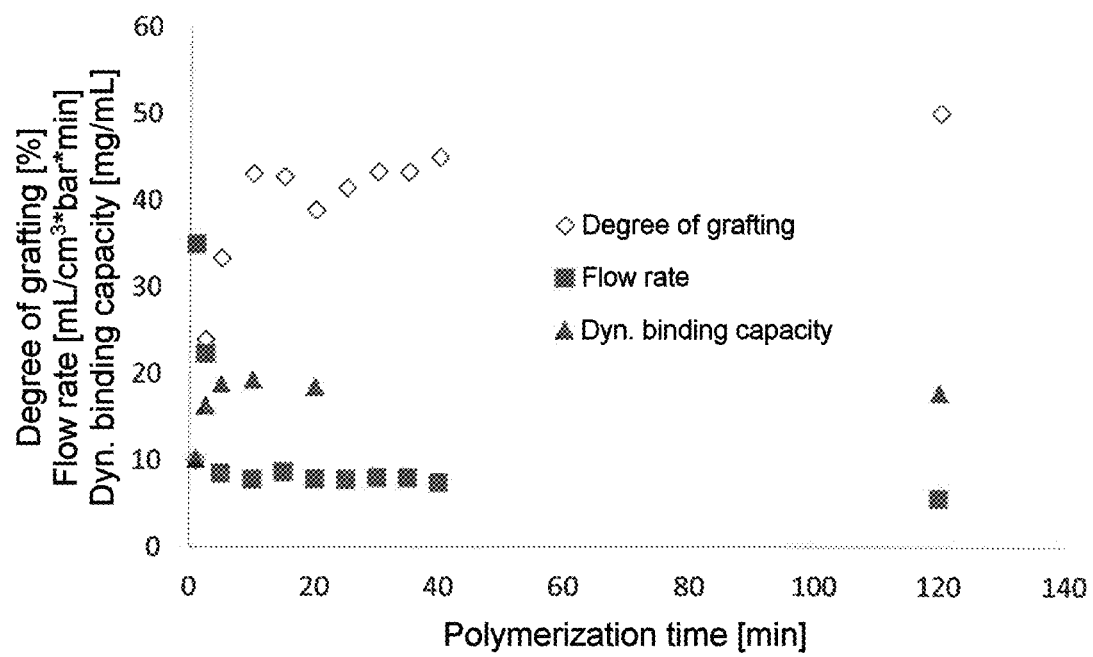
FIG. 8: Plot of the permeability (the flow rate), the degree of grafting and the dynamic binding capacity against the polymerization time of the modification.

FIG. 8 shows a plot of the permeability (flow rate), of the degree of grafting P and of the dynamic binding capacity of a protein A membrane adsorber for IgG against the polymerization time of the modification of a starting matrix. The degree of grafting can, in this connection, be adjusted both via the choice of components for the modification and via the reaction period. It is evident from FIG. 8 that the composition according to the invention allows very rapid reaction times which lead to the structural features according to the invention. As the polymerization time increases, the degree of grafting increases just as the permeability for water and the dynamic binding capacity for IgG decrease. In the case according to the invention, a high degree of grafting exhibits a maximum which, when exceeded, leads to a poorer performance of the chromatography medium. Especially the long polymerization time of 120 minutes, as disclosed in the PA documents, has exclusively adverse effects on the performance of the chromatography medium (see also Example 9).

As explained above, the degree of grafting can also be described as relative degree of grafting via the following equation:

$$P_{rel} = \frac{P * \rho}{Por}$$

where P is the above-defined degree of grafting of the chromatography medium in %, ρ is the density of the porous matrix without microglobules in g/cm³, and Por is the porosity of the porous matrix without microglobules in %.

Figure 9:
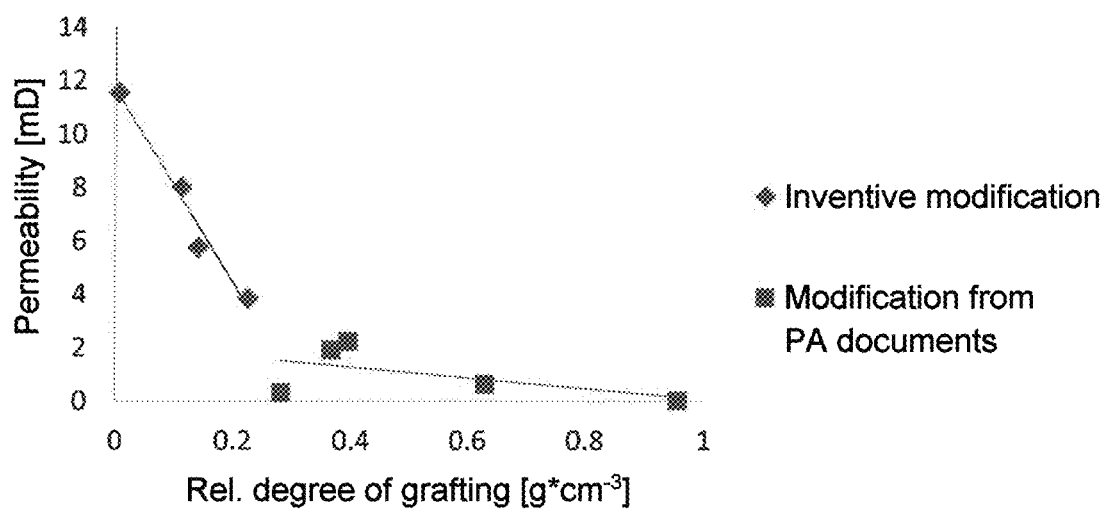
FIG. 9: Plot of the permeability against the relative degree of grafting.

FIG. 9 shows a plot of the permeability of chromatography media according to the invention (diamonds) and chromatography media from cited PA documents 1 to 5 (squares) against their respective relative degree of grafting. The relative degree of grafting of the chromatography media in cited PA documents 1 to 5 is more than 0.25 g/cm³, and this leads to a distinct decline in the permeability of the chromatography media. In contrast, the chromatography media according to the invention advantageously exhibit a higher permeability owing to their lower degree of grafting.

Moreover, the correlation between permeability and relative degree of grafting shows very clearly that the nonporous microglobules merely narrow the pores of the starting matrix of the chromatography medium according to the invention, since a linear correlation is found. Moreover, it is possible, by way of example, to show, on the basis of second measurement points of said linear correlation, a Hagen-Poiseuille behavior between the ascertained pore size and the flow rate (permeability):

The Hagen-Poiseuille equation describes in general the change in volumetric flow rate in the case of laminar steady flows through a pipe with change in the radius and the length of the pipe when the fluid and its properties remain unchanged. Since, according to the invention, the length of the membrane remains unchanged and merely the diameter of the pores narrows as a result of the modification with microglobules, it can be assumed here that the postulated behavior and the related structural nature of the chromatography medium according to the invention (nonporous microglobules which merely narrow the pores of the starting matrix and do not clog them), as postulated according to the invention, applies.

TABLE

Experimental pore sizes and flow-rate determination in comparison with the calculated flow-rate determination according to Hagen-Poiseuille.

|  | Starting matrix | Chromatography medium after inventive modification | | Medium after modification according to PA document | |
| --- | --- | --- | --- | --- | --- |
|  |  | 1 | 2 | 2 | 4 |
| Pore size [µm] | 0.41 | 0.27 | 0.35 | 0.186 | 0.31 |
| Experimental H$_2$O flow rate [ml/cm$^2$*bar*min] | 36 | 7 | 19 | 6 | 7 |
| Pore-size reduction factor | / | 0.658 | 0.853 | 0.53 | 0.75 |
| Calculated H$_2$O flow rate after modification according to Hagen-Poiseuille [ml/cm$^2$*bar*min] | 36 | 6.77 | 19.11 | 2.98 | 11.76 |

$$\dot{V} = \frac{\pi \cdot r^4 \cdot \Delta p}{8 \cdot \eta \cdot l}$$

As shown by the above table, calculated and experimental flow rate match very well in the case of the chromatography medium according to the invention, whereas this cannot be observed in the case of the chromatography media from the PA documents. What can be inferred from this is that the pores of the starting matrix are increasingly narrowed with increasing degree of grafting in the case of the inventive modification, whereas the macroporous gels completely fill the pores in the chromatography media from the PA documents, and the flow rate is thus determined by the porosity of the macroporous gels, since a linear behavior cannot be observed here. Moreover, the flow rate (the permeability) of the chromatography media in the PA documents is smaller than that of the chromatography media according to the invention.

Example 9

Determination of the Immobilized Chromatographically Active Centers (Ligands) on Affinity Adsorbers For the determination of an immobilized protein as chromatographically active center (ligand) per membrane area, use was made of a BCA (bicinchoninic acid) assay. To this end, punches (d=13 mm) were punched out from chromatography media according to the invention, and they were initially placed into Petri dishes (3 mL) and wetted with the BCA reagent (2 mL). The BCA reagent consisted of BCA Protein Assay Reagent A (Pierce Prod. No. 23221) and BCA Protein Assay Reagent B (Pierce Prod. No. 23224) in the ratio 50:1. Thereafter, the samples thus prepared were agitated on a shaking platform (80 rpm) for 60 minutes.

Figure 10:
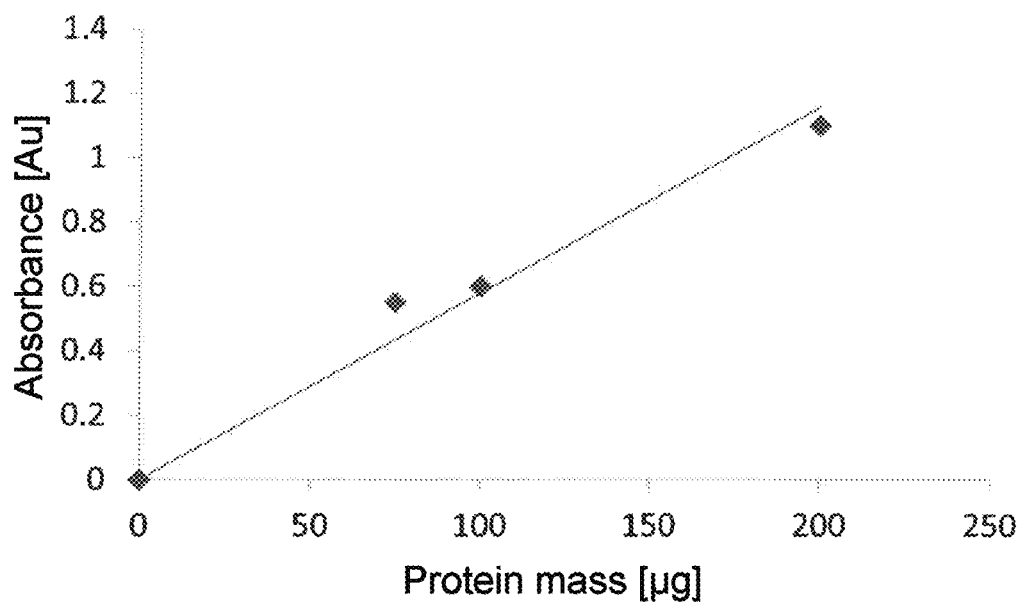
FIG. 10: Calibration curve for Example 9.

The color change resulting from the oxidation of the BCA reagent was measured as absorbance (at 562 nm) compared to a reference solution of the BCA reagent without membrane sample. The photometric measurements were done on a Specord 200 PLUS UV/Vis spectrophotometer from Analytik Jena. By means of the calibration curve from FIG. 10, which gave rise to the equation below, it was possible to convert the absorbance into protein mass [µg].

This value was subsequently related to the volume of the punch and specified in µg of protein per mL of membrane volume ($V_M$).

Protein $A$: $A[Au]=0.00578 \cdot lmm \cdot$ amount protein [µg]

Figure 11:
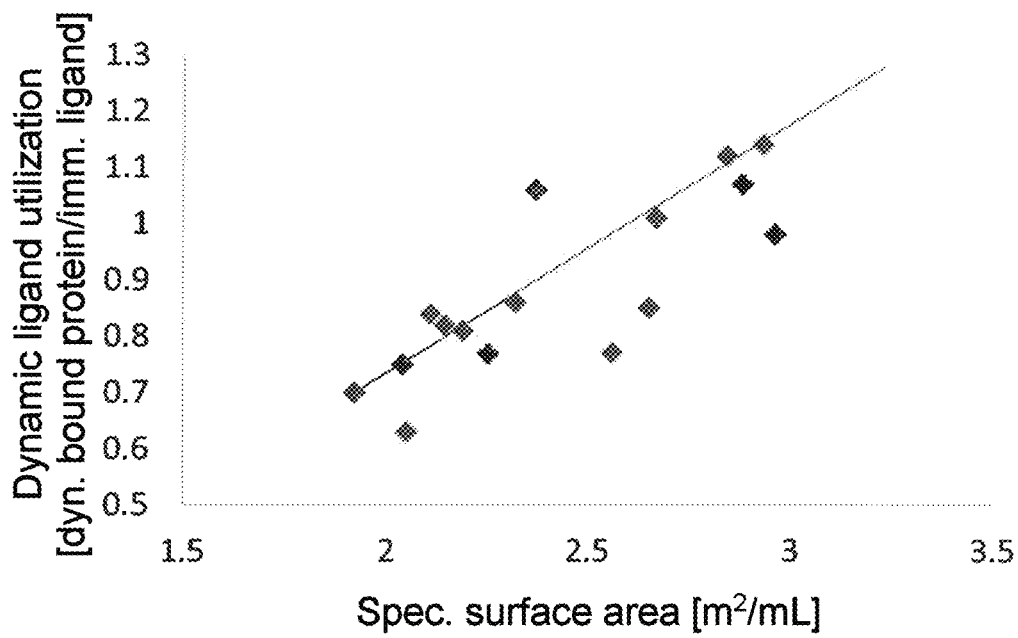
FIG. 11: Plot of the dynamic ligand utilization against the respective specific surface area of chromatography media according to the invention.
Figure 12:
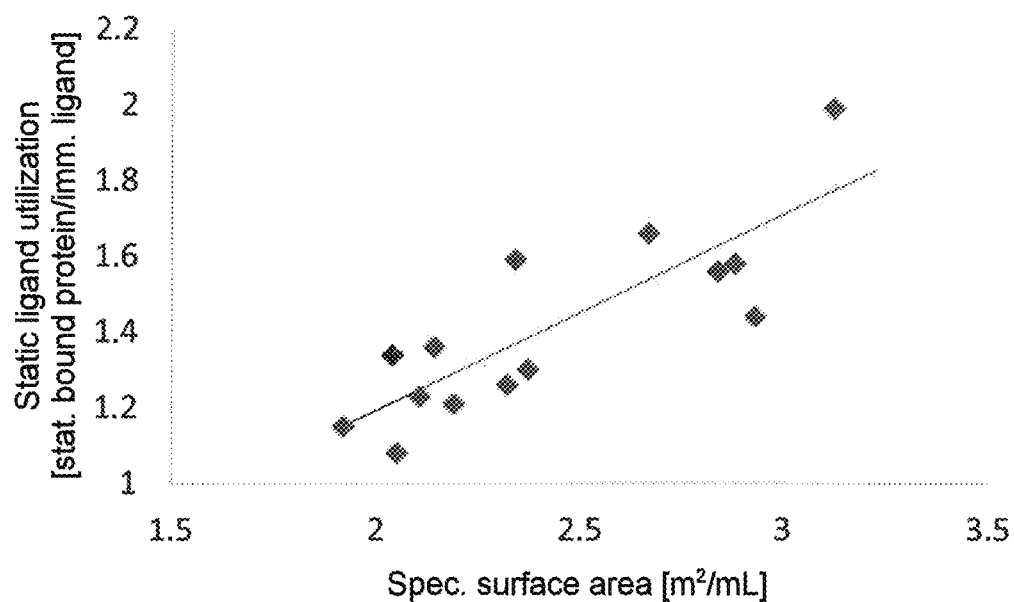
FIG. 12: Plot of the static ligand utilization against the respective specific surface area of chromatography media according to the invention.
Figure 13:
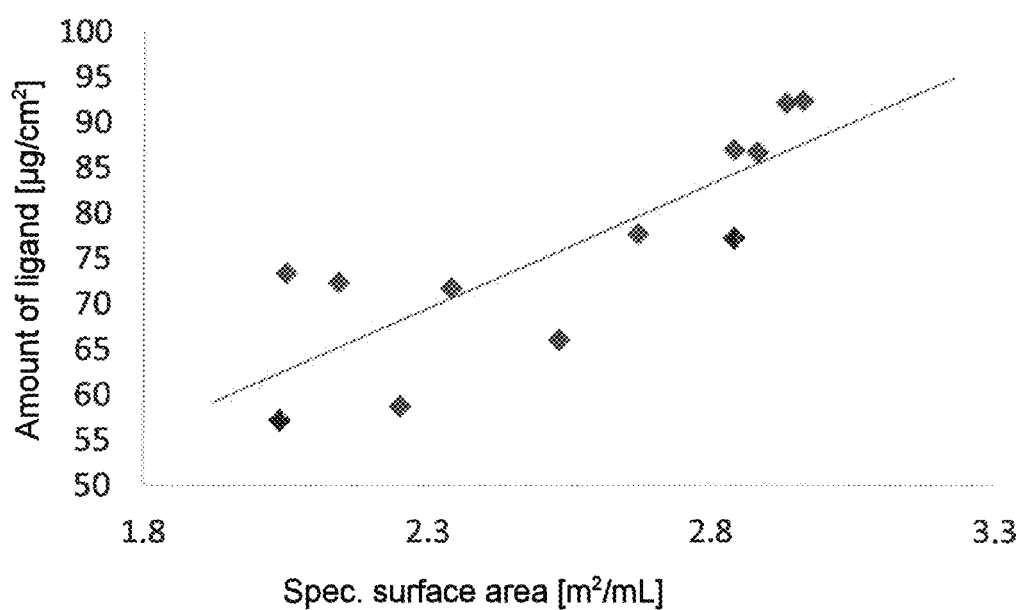
FIG. 13: Plot of the amount of immobilized ligand against the respective specific surface area of chromatography media according to the invention.

FIGS. 11 to 13 show plots of the dynamic ligand utilization (FIG. 11) and of the static ligand utilization (FIG. 12) and of the amount of immobilized ligand (FIG. 13) against the respective specific surface area of chromatography media according to the invention.

As can be identified in FIGS. 11 to 13, the larger specific surface area of the chromatography media according to the invention that is produced by the microglobules provides for a plurality of bound ligands and, surprisingly, for a better ligand utilization.

If the performance "Per" of chromatography media is defined as follows, the result is a distinct increase in performance compared to commercial affinity adsorbers and those from cited PA documents 1 to 5, as shown by the table below.

$$\text{Per} \left[\frac{mg \cdot mD}{mL}\right] = \text{Dyn. binding capacity}_{10\%} \left[\frac{mg}{mL}\right] \cdot \text{Permeability}_{H_2O} \text{ [mD]}$$

TABLE

Overview of the degree of grafting, the H$_2$O permeability, the dynamic binding capacity at 10% breakthrough (DBC$_{10\%}$) and the resultant performance of the chromatography media.

| Sample measured at 5 CV/min | Degree of grafting [%] | DBC$_{10\%}$ [mg/mL] | Permeability$_{H2O}$ [mD] | Per [mg*mD/mL] | Ligand utilization, dynamic$_{10\%}$/static |
| --- | --- | --- | --- | --- | --- |
| Inventive modification 1 | 40 | 21 | 2.7 | 56.70 | 1.5/2.0 |

TABLE-continued

Overview of the degree of grafting, the H₂O permeability, the dynamic binding capacity at 10% breakthrough ($DBC_{10\%}$) and the resultant performance of the chromatography media.

| Sample measured at 5 CV/min | Degree of grafting [%] | $DBC_{10\%}$ [mg/mL] | Permeability$_{H2O}$ [mD] | Per [mg*mD/mL] | Ligand utilization, dynamic$_{10\%}$/ static |
|---|---|---|---|---|---|
| Inventive modification 2 | 25 | 17 | 5.7 | 96.90 | 1.3/1.8 |
| Modification according to PA document 1 | 112 | 10 | 0.64 | 6.40 | 0.8/1.4 |
| Modification according to PA document 2 | 65 | 9 | 1.92 | 17.27 | 0.7/1.4 |
| Modification according to PA document 3 | 50 | 2 | 0.32 | 0.64 | 0.2/0.5 |
| Modification according to PA document 4 | 70 | 7 | 2.24 | 15.68 | 0.8/1.4 |
| Modification according to PA document No. 5 | 170 | 2 | 0.009 | 0.018 | 0.2/1 |
| Commercially available protein A membrane adsorber (Sartobind A - Sartorius Stedim Biotech GmbH) | / | 6 | 8.00 | 44.00 | 1/1.5 |

("5 CV/min" corresponds to a throughput of 5 column volumes per minute)

The invention claimed is:

1. A chromatography medium comprising:
   a porous matrix; and
   nonporous microglobules,
   the nonporous microglobules being bound on the inner and outer surfaces of the porous matrix by covalent means, and
   the average radius of the microglobules being not more than 30% of the average pore diameter of the porous matrix.

2. The chromatography medium as claimed in claim 1, wherein the permeability of the chromatography medium is at least 40% of the permeability of the porous matrix without bound microglobules.

3. The chromatography medium as claimed in claim 1, wherein the nonporous microglobules are substantially spherical oligomers and/or polymers which are constructed from at least one monomer selected from the group consisting of glycidyl (meth)acrylate, substituted or unsubstituted alkyl (meth)acrylates and their derivatives, styrene and its derivatives, 2-vinyl-4,4-dimethylazlactone, substituted or unsubstituted N-alkyl(meth)acrylamides and their derivatives and substituted or unsubstituted N-N'-dialkyl(meth)acrylamides and their derivatives.

4. The chromatography medium as claimed in claim 1, wherein the degree of grafting P of the chromatography medium is from 25% to 40%, given by:

$$P = \frac{m_m - m_0}{m_0} \cdot 100\%$$

where $m_m$ is the mass of the chromatography medium and $m_0$ is the mass of the porous matrix without microglobules.

5. The chromatography medium as claimed in claim 1, wherein the relative degree of grafting $P_{rel}$ of the chromatography medium is at most 0.25 g/cm³, given by:

$$P_{rel} = \frac{P * \rho}{Por}$$

where P is the degree of grafting of the chromatography medium in %, ρ is the density of the porous matrix without microglobules in g/cm³, and Por is the porosity of the porous matrix without microglobules in %.

6. The chromatography medium as claimed in claim 1, wherein the nonporous microglobules comprise additional chromatographically active centers or ligands which are bound to the microglobules or immobilized thereon.

7. A method for preparing a chromatography medium as claimed in claim 1, comprising:
   providing a porous starting matrix;
   providing a polymerization solution comprising at least one monomer, a bi-, tri- or multifunctional crosslinker, a polymerization initiator and a solvent or solvent mixture, the at least one monomer, the bi-, tri- or multifunctional crosslinker and the polymerization initiator being completely soluble in the solvent or solvent mixture; and
   initiating a polymerization in the polymerization solution in the presence of the porous starting matrix to form nonporous microglobules, the nonporous microglobules being insoluble in the solvent or solvent mixture and being bound to the inner and outer surfaces of the porous starting matrix by covalent means;
   the average radius of the microglobules being not more than 30% of the average pore diameter of the porous starting matrix.

8. The method for preparing a chromatography medium as claimed in claim 7, wherein the at least one monomer is selected from the group consisting of glycidyl (meth)acrylate, substituted or unsubstituted alkyl (meth)acrylates and their derivatives, styrene and its derivatives, 2-vinyl-4,4- dimethylazlactone, substituted or unsubstituted N-alkyl (meth)acrylamides and their derivatives and substituted or unsubstituted N-N'-dialkyl(meth)acrylamides and their derivatives.

9. The method for preparing a chromatography medium as claimed in claim 7, wherein the bi-, tri- or multifunctional crosslinker is selected from the group consisting of ethylene glycol dimethacrylate, trimethylpropane trimethacrylate, divinylbenzene and N-N-methylenebisacrylamide.

10. The method for preparing a chromatography medium as claimed in claim 7, wherein the polymerization initiator is selected from the group consisting of 2-hydroxy-4-(2-hydroxyethoxy)-2-methylpropiophenone, azobis(isobutyronitrile), 4,4-azobis(4-cyanovaleric acid), 1,1'-azobis(cyclohexanecarbonitrile), benzoyl peroxide, 2,2-bis(tert-butylperoxy)butane, 1,1-bis(tert-butylperoxy)cyclohexane, tert-butyl hydroperoxide, tert-butyl peroxyisopropyl carbonate, cyclohexanone peroxide and 2,4-pentanedione peroxide.

11. The method for preparing a chromatography medium as claimed in claim 7, wherein the solvent or solvent mixture is selected from the group consisting of cyclohexanol/dodecan-1-ol, octan-2-one, n-butyl acetate, p-xylene, toluene, ethyl acetate, benzonitrile, cyclohexanone, dodecan-1-ol, acetonitrile/ethanol/water, decan-1-ol and isopropanol/decan-1-ol.

12. The method for preparing a chromatography medium as claimed in claim 7, wherein the total volume of monomer and crosslinker, based on the total volume of the polymerization solution, is not more than 20% by volume.

13. The method for preparing a chromatography medium as claimed in claim 7, wherein the total volume of the crosslinker, based on the total volume of the polymerization solution, is not more than 6% by volume.

14. The method for preparing a chromatography medium as claimed in claim 7, wherein the concentration of the polymerization initiator in the polymerization solution is preferably from 1 to 3% by weight.

15. The method for preparing a chromatography medium as claimed in claim 7, wherein a macroscopically observable phase separation occurs after not more than 30 seconds.

* * * * *